United States Patent
Cheng et al.

(10) Patent No.: US 6,800,608 B2
(45) Date of Patent: Oct. 5, 2004

(54) HOMOGENEOUS ASSAY OF VANCOMYCIN USING A STABLE PARTICLE-VANCOMYCIN CONJUGATE, A NOVEL RATE ENHANCER, AND A NOVEL DOSE RESPONSE MODULATOR

(75) Inventors: Anthony K. Cheng, Anaheim, CA (US); Julie S. Kim, Placentia, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 190 days.

(21) Appl. No.: 09/888,005

(22) Filed: Jun. 22, 2001

(65) Prior Publication Data

US 2003/0077670 A1 Apr. 24, 2003

(51) Int. Cl.$^7$ .................................. A61K 38/00
(52) U.S. Cl. .................... 514/8; 514/2; 435/7.5; 436/533; 530/322
(58) Field of Search .................... 514/2, 8; 435/7.5; 530/322; 436/533, 815, 805

(56) References Cited

U.S. PATENT DOCUMENTS

| | | | |
|---|---|---|---|
| 4,134,792 A | 1/1979 | Boguslaski et al. | 195/99 |
| 4,238,565 A | 12/1980 | Hornby et al. | 435/7 |
| 4,670,258 A | 6/1987 | Harris et al. | 424/115 |
| 5,168,057 A | 12/1992 | Oh et al. | 435/174 |
| 5,196,351 A | 3/1993 | Harris et al. | 436/501 |
| 5,422,281 A | 6/1995 | Harris et al. | 436/501 |
| 5,627,080 A * | 5/1997 | Cheng et al. | 436/534 |
| 5,705,353 A | 1/1998 | Oh et al. | 435/7 |
| 5,705,535 A | 1/1998 | Jansen et al. | 521/64 |
| 5,747,352 A | 5/1998 | Yan et al. | 436/533 |

OTHER PUBLICATIONS

Yan et al. 1998, Biophysical Chemistry, vol. 74, No. 2, pp. 107–115.*
Mackey, et al., Glycopeptide Antibiotic Activity And The Possible Role Of Dimerization: A Model For Biological Signaling, J.Am. Chem. Soc., (1994), 116, 4581–4590.
Mackey, et al., Dissection Of The Contributions Toward Dimerization Of Glycopeptide Antibiotics, J. Am. Chem. Soc., (1994), 116, 4573–4580.
Ute Gerhard, et al., The Role Of The Sugar And Chlorine Substituents In The Dimerization Of Vancomycin Antibiotics, (1993), J. Am. Chem. Soc., 115, 232– 237.
Zheng Shi, et al., Catalysis Of Carbamate Hydrolysis By Vancomycin And Semisynthetic Derivatives, (1993), J. Am. Chem. Soc., 15, 6482–6486.
Popieniek, et al., Kinetics And Mechanism Of Binding Of Specific peptides To Vancomycin And Other Glycopeptide Antibiotics, (1991), J. Am. Chem. Soc., 113, 2264–2270.
Groves, et al., The Structure Of An Asymmetric Dimer Relevant To The Mode Of Action Of The Glycopeptide Antibiotics, (1994), Structure, vol. 2, No. 8, 747–754.

Waltho, et al., Aspects Of Molecular Recognition: Solvent Exclusion And Dimerization Of The Antibiotic Ristocetin When Bound To A Model Baterial Cell–Wall Precursor, (1989), J. Am. Chem. Soc., 111, 2475–2480.
Kannan, et al., Function Of The Amino Sugar And N–Terminal Amino Acid Of The Antibiotic Vancomycin In Its Complexation With Cell Wall Peptides, (1988), J. Am. Chem. Soc., 110, 294–2953.
Williams, et al., Molecular Basis Of The Activity Of Antibiotics Of The Vancomycin Group, (1988), Biochemical Pharmacology, vol. 37, No. 1, 133–141.
Nieto, et al., Modifications Of The Acyl–D–alanyl–D–alanine Terminus Affecting Complex–Formation With Vancomycin, (1971), 123, 789–803.
Costa Silva, V.L. et al., Aminoglycoside And Nephrotoxicity, (1987), Renal Physiol. 10: 327–337.
Fee, W.E. et al., Gentamicin And Tobramycin: Compaison Of Ototoxicity, (1983), Rev Infect. Dis. 5 (Suppl. 2): S304.
Lane, A.Z. et al., Ototoxicity And Nephrotoxicity Of Amikacin, (1977), Amer.J.Med. 62: 911.
Damien, J.M. et al., Amikacin Assay: Correlation Between Rapid Bioassay, Enzyme Immuno–Assay (EMIT) And Fluoro–Immuno–Assay (FIA), (1984), Ann. biol. Clin. 48: 217–220.
Sternberg, J.C., A Rate Nephelometer For Measuring Specific Proteins By Immunoprecipitin Reactions, (1977), Clin.Chem. 23: 1456–1464.
Mongkolsirichaikul, D. et al., Development Of A Latex Agglutination Inhibition Reaction Test For Amphetamines In Urine, (1993), J.Immunol, meth. 157: 189–195.
Paterson et al, A Radioimmunoassay For The Detection Of A Human Tumor Associated Glycoprotein (TAG–72) Using Monoclonal Antibody B72.3, (1986), Int. J.Can. 37: 659.
Burchell et al., Detection Of The Tumour–Associated Antigens Recognized By The Monoclonal Antibodies HMFG–1 And 2 In Serum From Patients With Breast Cancer, (1984), Int. J. Can. 34: 763.

* cited by examiner

Primary Examiner—Christopher R. Tate
Assistant Examiner—B. Dell Chism
(74) Attorney, Agent, or Firm—William H. May; D. David Hill; Hogan & Hartson, LLP

(57) ABSTRACT

This invention relates to stabilized formulations comprising a glycopeptide antibiotic immobilized on carrier particles, and more particularly stabilized vancomycin bidentate conjugate formulations for assaying the concentration of vancomycin in a test sample. The invention also relates to assay formats that utilize such stabilized formulations. The invention further provides a test kit for detecting the presence of vancomycin in a test sample, wherein the test kit includes a stabilized vancomycin conjugate formulation. The invention further provides a novel rate enhancer for immunoassays for enhancing the rate of binding of an anti-analyte antibody to the analyte.

28 Claims, 6 Drawing Sheets

LATEX-BASED BIDENTATE IMMUNOINHIBITION ASSAY – 2-REAGENT SYSTEM

HOMOGENEOUS ASSAY OF VANCOMYCIN USING A STABLE PARTICLE-VANCOMYCIN CONJUGATE, A NOVEL RATE ENHANCER, AND A NOVEL DOSE RESPONSE MODULATOR

FIELD OF THE INVENTION

This invention relates to reagents and methods for rapidly and quantitatively assaying the concentration of analytes in biological samples. More particularly, this invention includes stabilized vancomycin bidentate conjugates and other glycopeptide antibiotic bidentate conjugates and uses thereof in immunoassay formats for assaying the concentration of vancomycin in a test sample.

BACKGROUND OF THE INVENTION

The ability to determine the concentration of therapeutic agents in a biological sample is of broad importance in medicine. For example, glycopeptide antibiotics such as vancomycin, eremomycin, ristocetin A, etc., are clinically important in the treatment of post-surgical staphylococcal infections. However, even these otherwise beneficial drugs can induce life-threatening symptoms if abused or misdosed. Indeed, the adverse side-effects of these antibiotics, such as nephrotoxicity and ototoxicity, have been well-documented (Costa Silva, V. L. et al., *Renal Physiol.* 10:327–337 (1987); Fee, W. E. et al., *Rev Infect. Dis.* 5 (Suppl. 2):S304 (1983); Lane, A. Z. et al., *Amer. J. Med.* 62:911 (1977)). Thus, a narrow margin exists between the therapeutic dosage and toxicity-inducing overdosages (Witchitz, J. L. et al., *Nour. Presse Med.* 11:489–491 (1982); Damien, J. M. et al., *Ann. Biol. Clin.* 48:217–220 (1984). In view of the wide use of these therapeutic agents, and the importance of accurately assaying the concentration of antibiotics in patient samples, a variety of methods have been developed to permit the screening of large numbers of patients.

Immunoassays are assay systems that exploit the ability of an antibody to specifically recognize and bind to a particular analyte or "antigen." An antigen is a substance which is capable of inducing an immune response, i.e., antibody production, when introduced into an animal or human body. The region of an antigen that is recognized by an antibody and to which the antibody binds is referred to as an "epitope."Although large molecules such as proteins or other "antigens" possess multiple epitopes, low molecular weight molecules such as most pharmacological agents possess only a single epitope. Such low molecular weight molecules are referred to herein as "haptens."

The simplest immunoassay involves merely incubating an antibody that is capable of binding to a predetermined molecule (i.e., the "analyte") with a sample that is suspected to contain the analyte. The presence of the target molecule is determined by the presence, and is proportional to the concentration, of any immune complexes that form through the binding of antibody and the analyte. In order to facilitate the separation of such immune complexes from the unbound antibody initially present, a solid phase is typically employed. For example, in particle enhanced immunoassays, either the antibody or the antigen is immobilized on latex particles. The presence of the target molecule is then determined by incubating the immobilized antibody or antigen in the presence of the analyte-containing sample.

Target molecules that have become bound to the immobilized antibody can be detected in any of a variety of ways. For example, the support can be incubated in the presence of a labeled, second antibody (i.e., a "sandwich" immunoassay) that is capable of binding to a second epitope of the target molecule. Immobilization of the labeled antibody on the support thus requires the presence of the target, and is proportional to the concentration of the targets in the sample. In an alternative assay, the sample is incubated with a known amount of labeled targets and antibody binding sites. The presence of any target molecules in the sample competes with the labeled target molecules for the antibody binding sites. Thus, the amount of labeled target molecules that are able to bind the antibody is inversely proportional to the concentration of target molecules in the sample. This is known as a competitive immunoassay.

The various immunoassay formats can be further divided into two main classes depending upon whether the assay requires the separation of bound species from unbound species. Heterogeneous immunoassays require such purification and, hence, entail a separation or isolation step. In contrast, homogeneous assays are designed such that the removal of bound species from unbound species is unnecessary. Because homogeneous assays lack a separation step, and are more easily automated, they are more desirable than heterogeneous assays in applications that entail the screening of large numbers of patients.

If the immune complex is large enough, it will become capable of scattering light, or of spontaneously precipitating. In such cases, agglutination, nephelometric, or turbidimetric immunoassay methods may be employed. Nephelometric methods measure the light scattered by a suspension of particles or reflected toward a detector that is not in the direct path of light (Sternberg, J. C., *Clin. Chem.* 23:1456–1464 (1977)). In contrast, turbidimetric methods measure the reduction of light transmitted through the suspension of particles or aggregates. The reduction is caused by reflection, scatter, and absorption of the light by the aggregates. In both nephelometry and turbidimetry, the rate of change in light scatter may also be measured, and provides an indication of the amount of antigen present. Agglutination assays measure the precipitation of antibody-antigen complexes. Such assays can be extremely sensitive and are amenable to automation. Because nephelometric and turbidimetric methods do not require the separation of the initially present antibody from the immune complexes formed in the assay, such assays are homogenous immunoassays.

The requirement of producing large immune complexes has limited the applicability of nephelometric, turbidometric, or agglutination immunoassays to high molecular weight molecules, such as proteins, that possess several epitopes (i.e. antibody binding sites). In particular, many haptens such as therapeutic agents have only a single epitope and, as such, are incapable of forming the large immune complexes needed for such immunoassays.

Two approaches have been exploited to define agglutination assays for haptens. One approach is a particle enhanced immunoassay involving the agglutination of antibody-coated particles with a polyepitopic species or a developer antigen containing at least two covalently coupled hapten analogs (e.g., a protein carrier, such as BSA) (Mongkolsirichaikul, D. et al., *J. Immunol. Meth.* 157:189–195 (1993)). The agglutination reaction requires the use of a developer antigen or a polyepitopic species because a molecule that has only one epitopic site cannot bind two antibodies, and hence cannot cross-link two antibodies together. Such cross-linking is, however, an essential step in the formation of large immune complexes. The second particle enhanced approach involves the agglutination of hapten-coated particles and antibody for the agglutination reaction.

With either method, the hapten or drug in the sample competitively binds to the antibody binding sites and results in inhibition or reduction of the immunoagglutination. Particle agglutination assays for therapeutic drugs and drugs of abuse which use hapten-coated particles are commercially available. Examples of such assays are PETINIA (Du Pont) and AbuScreen (Roche), Advisor (Abbott) and that of Mitsubishi.

A third solution to this problem has recently been described by Yan, et al. in U.S. Pat. No. 5,747,352, which is incorporated herein by reference. Yan et al. disclose a particle-enhanced homogeneous assay for aminoglycoside antibiotics, including vancomycin. The method is based on a latex-avidin bidentate assay for vancomycin using a biotinylated vancomycin bidentate conjugated to an avidin-latex particle. In the bidentate immunoassay method described by Yan et al., the biotinylated vancomycin/avidin latex particle conjugate is incubated with an anti-vancomycin antibody and a test sample. The inhibition of agglutination between the conjugate and the antibody indicates the presence of vancomycin in the sample.

The development of an assay kit for vancomycin, however, has met with great difficulty since vancomycin is known to be chemically unstable. For example, vancomycin forms several degradation products in aqueous solution at about pH 7 after several days. See, for example, FIG. 1, which provides an HPLC plot of a vancomycin solution at pH 7 after standing several days, showing the presence of the degradation products CDP1-M (crystalline degradation product, major form) and CDP1-m (crystalline degradation product, minor form). Thus, vancomycin in assay kit calibrators breaks down into CDP products, resulting in the loss of potency of the calibrator. Since calibrators are used for the purpose of obtaining a calibration curve, the use of calibrators containing partially degraded vancomycin will result in incorrect assay results. Further, vancomycin will dimerize by hydrogen bonding upon standing in solution. As a result, vancomycin calibrator kits are usually shipped in lyophilized form as with the EMIT® assay, or in a frozen state as with those from Abbott for the TDx® System.

Intermolecular dimerization of vancomycin molecules presents another problem in particle-enhanced immunoassays which employ vancomycin-immobilized particles, since vancomycin dimerization leads to agglutination of the vancomycin-immobilized particles prior to their use in the assay.

Nα,Nβ-diacetyl-L-lysine-D-alanine-D-alanine (DALAA) is a tripeptide that is known to bind to free vancomycin. Other dipeptides and tripeptides such as acetyl-D-alanine-D-alanine (ADADA) and acetyl-D-leucine-D-alanine (ADLDA) are known to bind vancomycin, but with lower affinity constants. It is also known that dipeptide- or tripeptide-complexed vancomycin can dimerize in solution as well, forming, in the case of tripeptides, tripeptide-vancomycin—vancomycin-tripeptide complexes (Mackay, et al., J. Am. Chem. Soc., (1994) 116: 4581–4590; Mackay et al., J. Am. Chem. Soc., (1994) 116: 4573–4580; Gerhard, et al., J. Am. Chem. Soc., (1993) 115: 232–237; Zheng Shi, et al., J. Am. Chem. Soc., (1993) 115: 6482–6486; J. Am. Chem. Soc., Popieniek, et al., (1991) 113: 2264–2270; Groves, et al., Structure, (1994) vol. 2, No. 8, 747–754; Waltho, et al., J. Am. Chem. Soc., (1989) 111: 2475–2480; Kannan, et al., J. Am. Chem Soc., (1988) 110: 2946–2953; Williams, et al., Biochemical Pharmacology, (1988) vol. 37, No. 1, 133–141; Nieto et al., Biochem. J., (1971) 123:789–803). Mackay et al. (J. Am. Chem. Soc. (1994) 116: 4581–4590) have reported that while the dipeptide or tripeptide such as DALAA prevents or reduces vancomycin from forming CDP1 products, it also enhances the dimerization of vancomycin molecules, forming, in the case of dipeptides, dipeptide-vancomycin—vancomycin-dipeptide complexes.

There still exists a need for stabilized solutions of vancomycin-immobilized particles for assaying vancomycin in test samples. This need is met by the present invention, which provides stable vancomycin-immobilized particles, formulations comprising the stabilized particles and improved immunoassays employing such formulations.

SUMMARY OF THE INVENTION

This invention relates to novel stabilized formulations comprising glycopeptide antibiotics such as vancomycin immobilized on carrier particles and, more particularly, to methods for stabilizing glycopeptide antibiotic bidentate conjugate formulations for use in assaying glycopeptide antibiotics in a test sample. The invention also relates to assay formats that utilize such stabilized formulations. The glycopeptide antibiotic bidentate conjugates of this invention comprise glycopeptide antibiotics including, but not limited to, vancomycin, eremomycin, ristocetin A, and other glycopeptide antibiotics having structures similar to vancomycin.

Accordingly, one aspect of this invention provides methods for preparing stabilized vancomycin conjugate formulations, the method comprising:
  (a) forming a vancomycin conjugate comprising a vancomycin member bound to a ligand, the ligand being bound to a ligand-binding partner immobilized on a solid support, wherein the conjugate is formed under conditions that eliminate intermolecular hydrogen bonding between the vancomycin members;
  (b) mixing the conjugate with at least one stabilizing agent that prevents dimerization between vancomycin members, wherein the pH of the mixture is between about pH 7 to pH 9;
  (c) heating the mixture at a temperature between about 40° and 50° C. for about 3 to 14 days to ensure colloidal stability; and
  (d) storing the heat-treated mixture obtained in step (c) in a diluent buffer having a pH of about 6.5–8.5.

Another aspect of the present invention provides stabilized vancomycin conjugate formulations prepared according to the method of this invention, comprising:
  a) a bidentate conjugate comprising a vancomycin member bound to a ligand, the ligand being bound to a ligand-binding partner immobilized on a solid support; and
  b) at least one stabilizing agent that prevents dimerization between vancomycin members, wherein the bidentate conjugate and the stabilizing agent are dissolved in a diluent buffer having a neutral pH.

The stabilized vancomycin conjugate formulations of the present invention may be used in particle enhanced immunoassays for the detection of vancomycin in a sample. The stabilized vancomycin conjugate formulations are particularly suited for competitive immunoassays. Accordingly, another aspect of the present invention provides an immunoassay for the detection of vancomycin in a test sample, comprising:

(a) providing a stabilized vancomycin conjugate formulation comprising:
  (i) a bidentate conjugate comprising a vancomycin member bound to a ligand, the ligand being bound to a ligand-binding partner immobilized on a solid support; and
  (ii) at least one stabilizing agent that prevents dimerization between vancomycin members, wherein the bidentate conjugate and the stabilizing agent are dissolved in a conjugate diluent having a neutral pH;
(b) providing an antibody that is immunoreactive with vancomycin;
(c) mixing the sample with the vancomycin conjugate formulation and the antibody to form a reaction mixture;
(d) incubating the reaction mixture under conditions that allow binding of the antibody to the vancomycin contained in the sample or the vancomycin member of the bidentate conjugate; and
(e) determining the amount of the vancomycin member of the bidentate conjugate that bound with the antibody, wherein the amount is inversely proportional to the concentration of the vancomycin in the sample.

The present invention further provides a test kit for use in an immunoassay for determining the amount of vancomycin in a test sample, wherein one of the components of the test kit is a stabilized vancomycin conjugate formulation of this invention.

The invention further provides a novel rate enhancer for enhancing binding between an analyte in a test sample and an anti-analyte antibody in an immunoassay. The rate enhancer is particularly useful in particle-enhanced immunoassays.

The invention further provides a novel dose-response modulators for use in immunoassays. The dose-response modulators enable modulation of immunoassay sensitivity so as to obtain an assay that exhibits a more desirable reaction rate and dose response.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

BRIEF DESCRIPTION OF THE FIGURES

The accompanying drawings, which are incorporated herein and form a part of the specification, illustrate preferred embodiments of the present invention and, together with the description, serve to explain the principles of the invention.

In the Figures.

DETAILED DESCRIPTION OF THE INVENTION

Figure 1:
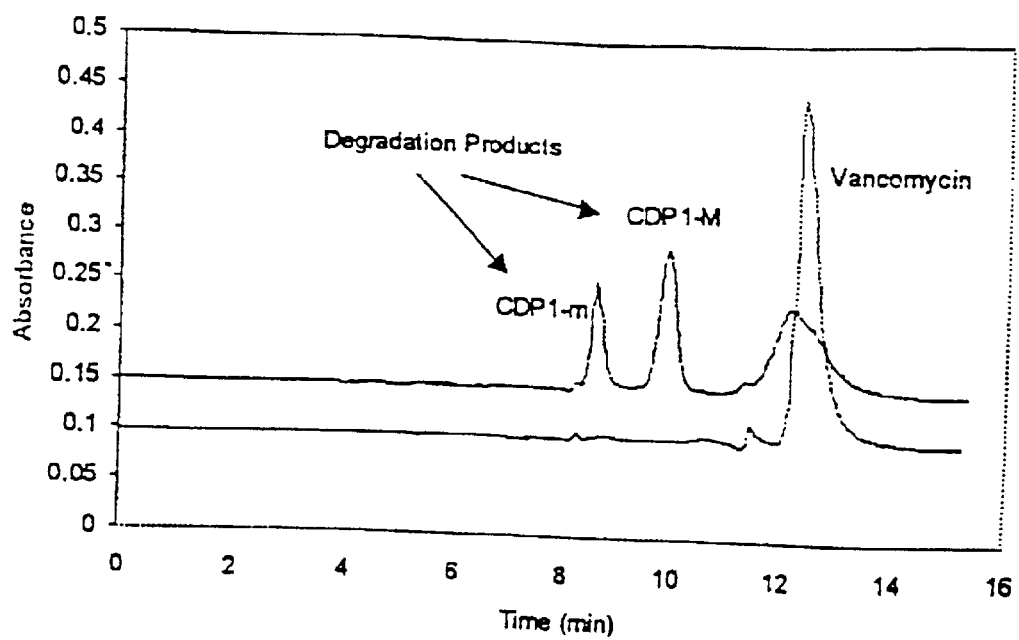
FIG. 1 is an HPLC plot of vancomycin in an aqueous solution at about pH 7 after seven days at 45° C., showing the formation of the degradation products CDP1-M and CDP1-m.
Figure 2:
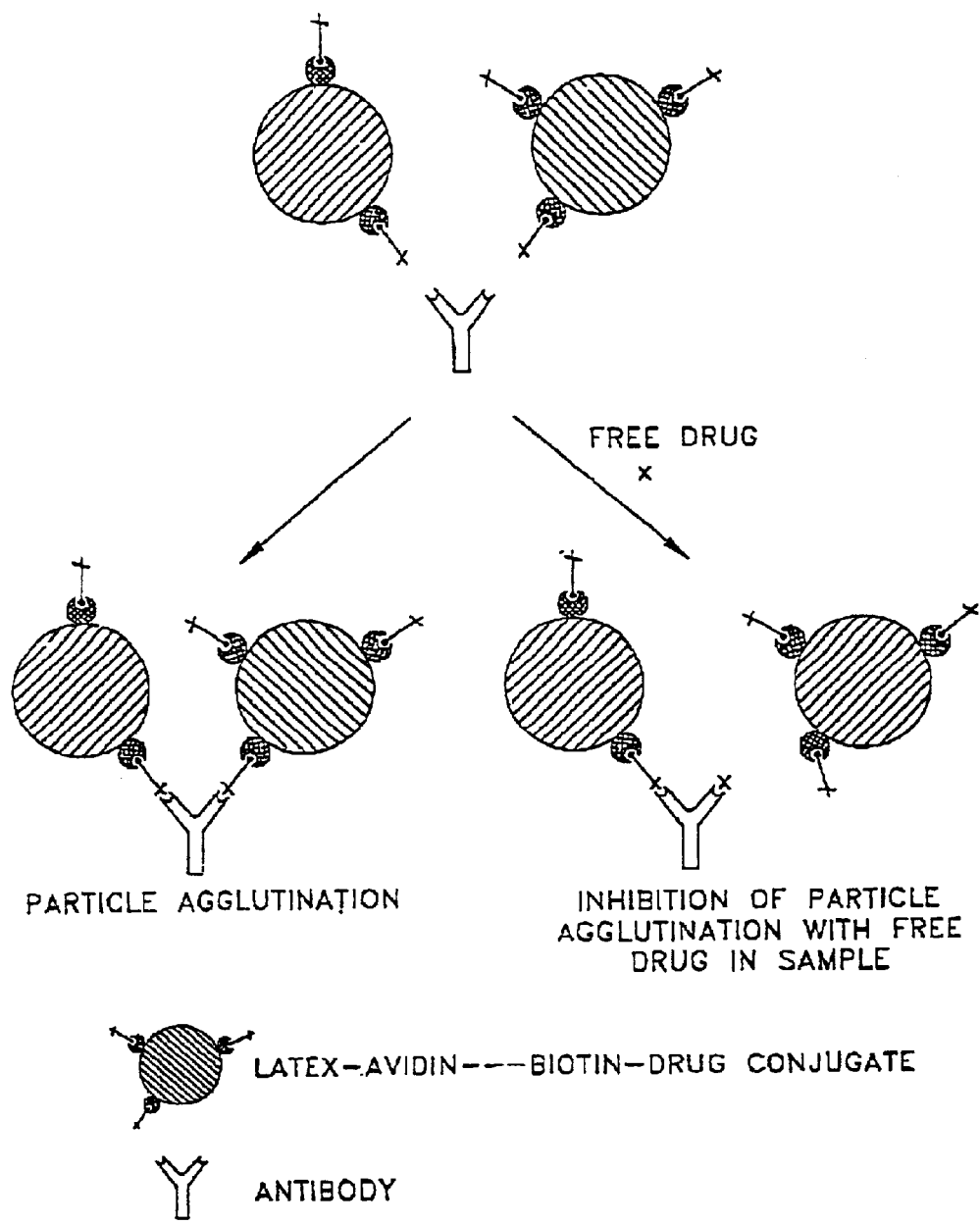
FIG. 2 shows a diagrammatic representation of a particle-enhanced immunoassay of the present invention.

This invention relates to novel stabilized formulations comprising glycopeptide antibiotics such as vancomycin immobilized on carrier particles and, more particularly, to methods for stabilizing glycopeptide antibiotic bidentate conjugate formulations for use in assaying glycopeptide antibiotics in a test sample. The glycopeptide antibiotic bidentate conjugates of this invention comprise glycopeptide antibiotics including, but not limited to, vancomycin, eremomycin, ristocetin A, and other glycopeptide antibiotics having structures similar to vancomycin. The invention also relates to immunoassay formats that employ such stabilized formulations.

While this invention is describe in detail with respect to the stabilization of formulations wherein the antibiotic is vancomycin, it is to be understood that such description is for ease of explanation and is not meant to be limiting in any way. Thus, the scope of this invention includes the stabilization of all glycopeptide antibiotic conjugate formulations, wherein the glycopeptide antibiotics have structures similar to vancomycin. Such antibiotics include, but are not limited to, eremomycin, ristocetin A, and other glycopeptide antibiotics sharing similar heptapeptide backbones carrying one or more sugar substituents.

This invention provides an improvement over conventional particle-enhanced methods for assaying glycopeptide antibiotics such as vancomycin. For example, the vancomycin bidentate conjugate of this invention for use in such assays are stabilized in part by combining the conjugate a stabilizing agent that prevents dimerization of the vancomycin members of the bidentates. The stabilizing agent is believed to prevent dimerization by preventing intermolecular hydrogen bonding between vancomycin members. As a result of the addition of the stabilizing agent, massive particle aggregation of vancomycin conjugates due to vancomycin dimerization is prevented.

As indicated, Yan et al. (U.S. Pat. No. 5,747,352) describe the immobilization of bidentate reagents on macroscopic particles for the detection of pharmacological agents such as vancomycin in immunoassay formats. However, the conjugates prepared by Yan et al. were used immediately after their preparation, and Yan et al. do not provide any method of preparing such conjugates that are stable for longer periods of time. The present invention is an improvement of Yan et al. (U.S. Pat. No. 5,747,352) by providing a method for stabilizing these vancomycin conjugates to provide stabilized vancomycin conjugate formulations. The formulations of this invention are stable for at least 7 days at 45° C.

Accordingly, one aspect of this invention provides a method of stabilizing a vancomycin conjugate formulation, comprising:

(a) forming a bidentate conjugate comprising a vancomycin member bound to a ligand, the ligand being bound to a ligand-binding partner immobilized on a solid support, under conditions that minimize intermolecular hydrogen binding between the vancomycin members;

(b) mixing the bidentate conjugate with at least one stabilizing agent that prevents dimerization between vancomycin members, wherein the pH of the mixture is between about pH 7 to pH 9;

(c) heating the mixture at a temperature between about 40° and 50° C. for about 3 to 14 days to ensure colloidal stability; and (d) storing the heat-treated mixture obtained in step (c) in a diluent buffer having a pH of about 6.8 to 8.5, preferably at a pH of about 7.0 to 7.5.

The method of this invention for stabilizing a vancomycin conjugate first comprises forming a bidentate conjugate comprising a vancomycin member bound to a ligand as in step (a) above, wherein the ligand is immobilized on a solid support via a ligand-binding partner. More specifically, in accordance with one embodiment of the present invention, the method for forming the bidentate conjugate as recited in step (a) above comprises:

(i) preparing a ligand binding partner immobilized on a solid support;

(ii) preparing a vancomycin bidentate comprising a vancomycin member bound to a ligand through a spacer molecule;

(iii) coupling the ligand to the immobilized ligand-binding partner to form a bidentate conjugate under alkaline conditions that avoid aggregation of the vancomycin conjugate; and (iv) isolating the bidentate conjugate under alkaline conditions to minimize intermolecular hydrogen bonding between vancomycin members.

Step (i) in the preparation of the bidentate reagent comprises immobilizing a ligand binding partner on a solid support. For ease of explanation, the method of preparing a vancomycin bidentate conjugate of this invention will be described using biotin as the ligand and a biotin binding partner as the ligand binding partner. In this example, a biotin binding partner includes, but is not limited to, avidin, streptavidin, and anti-biotin antibodies or antibody fragments thereof.

As used herein, the terms "ligand" refers to a small molecule or chemical moiety, and is one example of a bidentate member. The ligand may be naturally occurring or it may be artificially prepared. A ligand is capable of specifically binding to a ligand binding partner.

For purposes of this invention, the terms "ligand binding partner" and "specific binding partner" are used interchangeably and refer to a molecule or substance that specifically binds to a ligand. The specific binding partner has a specific binding affinity for the ligand to the exclusion of other substances. Such binding molecules specific for a given ligand may be obtained from commercial sources or may be prepared in accordance with standard procedures known to those skilled in the art. Examples of ligand:specific binding partner pairs include, but are not limited to, hapten:antibody, biotin:avidin, hormone:receptor, polypeptide:antibody, and oligonucleotide:complementary DNA or RNA.

As used herein, the term "biotin binding partner" refers to ligand binding partner that recognizes and binds to biotin. Biotin binding partners include, but are not limited to, anti-biotin antibodies (or fragments of such antibodies), streptavidin, and avidin.

Step (i) provided above in the preparation of the bidentate conjugate comprises immobilizing the biotin-binding partner to a solid support. The solid supports employed are insoluble carrier particles including, but not limited to, latex particles, magnetic particles, colloidal metals and colloidal metal oxides. These and other suitable carrier particles which may be used in this invention are well-known to those skilled in the art. The particles may be coated with dyes to aid in separation or detection of the particles. Preferably the carrier particles are latex particles.

For ease of explanation, the preparation of the bidentate conjugate will further be described using avidin as the biotin binding partner and latex particles as the solid support. However, those of ordinary skill in the art will appreciate that other binding partners and other solid support materials may be used in the method of this invention. Thus, using avidin as an example, the term "immobilized" refers to an avidin that is chemically coupled to the latex particles through covalent bonds. However, it is to be understood that the term "immobilized" may also refer to non-chemical methods for immobilizing a ligand binding partner to a carrier particle, such as through physical adsorption (i.e., through non-covalent bonds).

There are many methods known in the art for coupling avidin to latex particles. One preferred method of this invention comprises coupling avidin to carboxylated latex particles following the procedure described by Yan et al in U.S. Pat. No. 5,747,352, which is specifically incorporated herein by reference. The preferred coupling procedure according to Yan et al. involves two steps: the activation of carboxyl groups of the latex particles with carbodiimide and N-hydroxysuccinimide, followed by reaction of the activated particles with avidin. Since avidin has an isoelectric point (pI) of 10, the pH of the second step of the reaction is preferably maintained slightly basic (pH 8.5 to 9). Such conditions ensure that a sufficient number of avidin molecules will remain in their free base form, and will thus be available for nucleophilic reaction with the activated carboxylated groups on the latex particles. At pH 8 or lower, non-specific aggregation of latex particles may occur as soon as avidin is added, possibly due to the charge interactions between avidin and the latex particle or the capture of the particles by avidin via physical adsorption. Overloading the particles with avidin at pH 8.5 to 9 can also result in non-specific particle aggregation.

For purposes of this invention, the term "non-specific aggregation" refers to the aggregation of particles in a manner that does not involve binding between an analyte in the test sample and its binding partner immobilized on the insoluble particles. For example, non-specific particle aggregation may occur as a result interaction between the positive charge of an avidin molecule immobilized on one particle with the negative charge of the carboxyl group on a second particle.

Briefly, in one embodiment the avidin-labeled particles are produced by incubating latex particles in the presence of N-hydroxysuccinimide and carbodiimide at 4° C. as disclosed in U.S. Pat. No. 5,747,352. The pH of the mixture is then raised to about 9.0, and avidin is added. The latex-avidin complex can be recovered by chromatographic means (such as by Sepharose CL-6B purification, or ultrafiltration using large pore membranes), preferably after dialysis to remove the coupling reagents.

In one embodiment, the latex-avidin particles are heat-stressed for between about 2 and 10 days, preferably for 3 to 6 days at a temperature between about 30 and 50° C., preferably at 45° C., prior to coupling the particles to the bidentate. Heat-stressing is known to enhance the immunoreactivity and assay sensitivity in terms of steeper dose response.

Step (ii) above in the preparation of the vancomycin bidentate conjugate comprises preparing a vancomycin bidentate. The preparation of a vancomycin-biotin bidentate will be described for purposes of illustration. However, it will be appreciated by those skilled in the art that other vancomycin bidentates may be used in the methods of this invention.

The term "bidentate" refers to a heterobifunctional conjugate having two different chemical moieties, or bidentate members, which function as small molecule ligands and are attached through an adequate spacer moiety. The two small molecule ligands, or "bidentate members," are each capable of specifically binding to a different specific binding partner. The spacer is of sufficient length to allow simultaneous binding of both bidentate members to their specific binding members at the same time. The binding of one specific binding partner may, in fact, occur prior in time to the binding of the other specific binding partner.

The term "bidentate conjugate" are used refers to a bidentate wherein one of the bidentate members is further bound to a solid support via a specific binding partner for that bidentate member. One example of a bidentate conjugate of this invention is a vancomycin conjugate comprising a vancomycin-biotin bidentate, wherein the biotin is bound to a biotin binding partner, wherein the biotin binding partner is bound to an solid support.

Many methods have been described in the art for linking together the two members of a bidentate through a spacer member to form a bidentate such as a vancomycin-biotin bidentate. See, for example, U.S. Pat. No. 5,196,351, U.S. Pat. No. 4,134,792, and U.S. Pat. No. 4,238,565, all of which are specifically incorporated herein by reference. These methods generally involve typical condensation, addition, and substitution reactions between chemical moieties which may or may not have been activated prior to such reactions.

As disclosed by Harris, P. C. et al. (U.S. Pat. No. 5,196,351), spacers of about 20 atoms are capable of tethering the members of a bidentate to one another without adversely effecting their respective capacities to bind to their binding partners. Longer or shorter spacers can, however, be employed. The particular chemical composition of the spacer moiety will depend, to some extent, on the nature of the chemical sites available on the respective bidentate members for connecting the spacer moiety.

The precise method used to link the bidentate members together through the spacer moiety is not critical. What is important is that the spacer is of adequate length to allow both bidentate members to effectively and simultaneously bind with their specific binding partners in a homogeneous assay.

After preparation of both the avidin-latex particles and the vancomycin-biotin bidentate, these two components are coupled to form the vancomycin conjugate as provided in step (iii) above. The coupling of avidin-latex particles with analyte-biotin bidentates to prepare bidentate conjugates has been described by Yan et al. in U.S. Pat. No. 5,747,352, which is specifically incorporated herein by reference. In the method described by Yan et al., the latex-avidin particles are preincubated with the bidentate under conditions of bidentate excess, such that substantially all of the biotin binding sites are filled with the biotin member of the bidentate. Subsequently, the excess bidentate is removed by size exclusion column chromatography, dialysis, or other means.

However, as described above, vancomycin tends to dimerize via intermolecular hydrogen bonding. Consequently, the inventors of the present invention discovered that the particular conditions used to prepare and isolate vancomycin bidentate conjugates are critical in order to prevent dimerization of the vancomycin members.

First, the inventors discovered that the step involving the coupling the vancomycin bidentate with latex-avidin particles to form the vancomycin conjugate must be conducted at alkaline pH, preferably with a buffer at about pH 9, to avoid intermolecular hydrogen bonding and subsequent dimerization of the vancomycin members during the coupling reaction.

Further, the inventors discovered that it is preferable to isolate the vancomycin conjugate as provided in step (iv) above under conditions that prevent intermolecular hydrogen bonding between vancomycin members, and thus avoid dimerization of the vancomycin members leading to particle aggregation. In one embodiment, the vancomycin conjugate is isolated by removing excess vancomycin bidentate by a suitable method such as diafiltration using a buffer at an alkaline pH, preferably at about pH 8–10, more preferably at about pH 9. Suitable buffers include, but are not limited to, TRIS, phosphate and borate buffers. The vancomycin conjugate is thus isolated in this alkaline medium. Other suitable methods may be used to isolate the vancomycin conjugate, provided that the isolation methods are performed under alkaline conditions. Other isolation methods known to those skilled in the art are included for purposes of this invention. Such isolation methods include, but are not limited to, dialysis and sized exclusion chromatography.

Increasing the pH both during the coupling reaction and the purification of the vancomycin conjugate serves to reduce or eliminate intermolecular hydrogen bonding and subsequent dimerization of the vancomycin members, thereby preventing massive particle aggregation of vancomycin conjugates.

The isolation of the vancomycin conjugate is followed by the addition of at least one stabilizing agent to a solution of the conjugate to enhance the stability of the conjugate solution by preventing dimerization between vancomycin members of the conjugates.

As used herein, a "stabilizing agent" refers in general to any compound or material that interacts with a glycopeptide antibiotic member of a conjugate to prevent dimerization between glycopeptide antibiotic members. For example, a stabilizing agent prevents dimerization between two vancomycin members of a vancomycin conjugate. Consequently, the stabilizing agent prevents particle aggregation as a result of dimerization between vancomycin members of vancomycin conjugates. Any stabilizing agent that can prevent dimerization of two glycopeptide antibiotic members of a glycopeptide antibiotic conjugate is suitable for purposes of this invention. Preferred stabilizing agents include, but are not limited to, the tripeptide N$\alpha$,N$\beta$-diacetyl-L-lysine-D-alanine-D-alanine (DALAA; BaChem, Torrance, Switzerland, cat. No. M-1325; and Sigma, St. Louis, Mo., cat. No. D9904) and heparin, (Scientific Protein Laboratory, Waunakee, Wis.).

As stated above, while DALAA is known to chemically stabilize free vancomycin molecules in solution by preventing DALAA from breaking down into the degradation products CDP1-M and CDP1-m, it is also known that DALAA enhances the dimerization of free vancomycin.

However, the inventors of the present invention surprisingly and unexpectedly discovered that DALAA prevents dimerization of vancomycin members of vancomycin conjugates and, consequently, the addition of DALAA to a vancomycin conjugate solution was discovered to provide a stabilized vancomycin conjugate formulation. The amount of DALAA added to the vancomycin conjugate solution is preferably between about 0.05 and 0.25 milligrams per milliliter of the conjugate. Other suitable vancomycin complexing agents which may be used as stabilizing agents in this invention include dipeptides and tripeptides that bind to vancomycin, including but not limited to acteyl-D-alanine-D-alanine (ADADA) and acetyl-D-alanine-D-alanine-D-alanine (ADADADA).

Another stabilizing agent that may be used to prepare stabilized vancomycin conjugate formulations of this invention is heparin. Heparin is a negatively charged glycosaminoglycan which prevents dimerization possibly by disrupting hydrogen bonding between vancomycin members. The addition of heparin to particle enhanced assay reaction mixtures was disclosed in U.S. Pat. No. 5,705,535, specifically incorporated herein, as a method of masking the effects of an interfering substance such as heparin present in heparinized sample. The inventors of the present invention discovered that heparin can also be used as a stabilizer in the conjugate formulations of the present invention. Thus, the addition of heparin to a vancomycin conjugate solution also serves to provide a stabilized vancomycin conjugate formulation. The amount of heparin added to the formulation is preferably between about 500 and 2000 units. Preferably heparin is used as a stabilizer in formulations used for testing heparinized samples such as blood, serum, and plasma.

The inventors discovered that the addition of one or more stabilizing agent to a vancomycin conjugate significantly enhances the stability of the vancomycin conjugate by preventing dimerization of the vancomycin members. In one preferred embodiment, the stabilizing agent is DALAA. In another preferred embodiment, the stabilized formulations of the present invention include both DALAA and heparin as stabilizing agents.

For purposes of this invention the term "stabilized vancomycin conjugate formulation" refers to a vancomycin conjugate formulation that is prepared and stored according to the methods of this invention, wherein vancomycin members are prevented from dimerizing with each other.

After the stabilizing agent is added to the vancomycin conjugate, the mixture is heat pretreated to ensure colloidal stability. For purposes of this invention, a mixture has "colloidal stability" if the vancomycin conjugate stays as a suspension in solution, that is, the vancomycin conjugate does not settle out of solution. In one embodiment, the vancomycin conjugate solution is heated at a temperature between about 40° C. and 50° C., preferably about 45° C., for about 3 to 14 days, wherein the pH of the solution is between about pH 7 or 9, preferably pH 7.5. After heat pretreatment, the conjugate formulation is stored in a conjugate diluent having a neutral pH. For purposes of this invention, the term "neutral pH" refers to a pH range of about pH 7 to 8.0. The pH of the conjugate diluent buffer should be close to neutral when the stabilizing agent DALAA is used, since a higher pH could result in instability of the tripeptide and, hence, the vancomycin conjugate upon long exposure to heat.

The method according to this invention thus results in the formation of a stabilized vancomycin formulation. Accordingly, another aspect of the present invention provides a stabilized vancomycin conjugate formulation comprising:

(a) a bidentate conjugate comprising a vancomycin member bound to a ligand, the ligand being bound to a ligand-binding partner immobilized on a solid support; and (b) at least one stabilizing agent that prevents dimerization of vancomycin, wherein the bidentate conjugate and the stabilizing agent are dissolved in a diluent buffer having a neutral pH.

The stabilized vancomycin conjugate formulations of the present invention may be used in particle enhanced immunoassays for the detection of vancomycin in a sample. The stabilized vancomycin conjugate formulations are particularly suited for competitive immunoassays. Accordingly, another aspect of the present invention provides an immunoassay for the detection of vancomycin in a test sample, comprising:

(a) providing a stabilized vancomycin conjugate formulation;

(b) providing an antibody that is immunoreactive with vancomycin;

(c) mixing the sample with the vancomycin conjugate formulation and the antibody to form a reaction mixture;

(d) incubating the reaction mixture under conditions that allow binding of the antibody to the vancomycin contained in the sample or the vancomycin member of the bidentate conjugate; and (e) determining the amount of the vancomycin member of the bidentate conjugate that bound with the antibody, wherein the amount is inversely proportional to the concentration of the vancomycin in the sample.

As used herein, the terms "sample" or "test sample" are used interchangeably and refer to a material suspected of containing an analyte of interest. The test sample can be untreated (undiluted), or chemically and/or physically treated, diluted, or concentrated prior to analysis. Examples of samples include, but are not limited to, samples from biological sources such as physiological fluids, including blood, plasma, serum, saliva, cerebral spinal fluid, urine, and amniotic fluid, and any other type of fluid, tissue or material which is suspected of containing an analyte of interest.

The general methods of the in vitro detection of analytes in fluid samples by competitive immunoassay procedures are well-known in the art and need not be described in detail here. For example, immunoassay procedures are generally described in "The Immunoassay Handbook", ed. D. Wild, Stockton Press (1994), Paterson et al., *Int. J. Can.* 37:659 (1986) and Burchell et al., *Int. J. Can.* 34:763 (1984). In one embodiment, a competitive immunoassay of this invention for the detection of vancomycin in a test sample comprises contacting the sample with a stabilized vancomycin conjugate formulation and an antibody that is immunoreactive with vancomycin under conditions that allow formation of an immune complex between the antibody and the vancomycin in the sample or the vancomycin member of the conjugate. An "immune complex" refers in general to a complex formed upon a reaction between an antigen and antibody. Particle aggregation resulting from the formation of the immune complex between the antibody and the vancomycin conjugate results in increased turbidity in the reaction medium.

The term "aggregation" refers generally to a process whereby individual analyte-immobilized particles or antibody-immobilized particles are linked together by antibodies or analytes, respectively, present in a sample being analyzed, to produce aggregates of particles, such as dimers, trimers, and higher order networks of aggregated particles. For example, in one embodiment of this invention, aggregation refers to the linking of two or more vancomycin conjugates via an anti-vancomycin antibody.

In a competitive assay of this invention for quantitation of vancomycin in a test sample, aggregation of the particles occurs to an extent dependent on the amount of vancomycin present in the sample. That is, vancomycin analyte present in the sample will compete with the vancomycin member of the conjugate for the antibody. An increase in binding of the vancomycin analyte with antibody results in a decrease in the binding of the vancomycin conjugate with the antibody. This in turn reduces particle aggregation, resulting in a decrease in turbidity. Thus, the presence and/or concentration of vancomycin analyte in a sample can be determined by detecting a change in turbidity of the reaction mixture. In competitive immunoassays, the extent of particle aggregation is inversely proportional to the amount of vancomycin present in the test sample.

The extent of aggregation in the immunoassay reaction mixture can be determined visually or with the use of an appropriate instrument. In one embodiment, the extent of aggregation is measured using conventional procedures, such as turbidimetry, nephelometry, conventional light scattering techniques, quasielastic scattering methods, angular anisotropic scattering determination or particle counting. Such methods are well-known, and one skilled in the art can select methods for measuring the extent of aggregation in an immunoassay reaction without undue experimentation. The aggregation measurement is then correlated to the amount of vancomycin in the test sample. In one embodiment, nephelometry or turbidity methods are used, as described by Oh et al. (U.S. Pat. No. 5,168,057) and Harris et al. (U.S. Pat. No. 5,196,351), which are specifically incorporated herein by reference. In these methods, the nephelometric or turbidimetric response can be measured by the rate or end-point method. The amount of vancomycin present can be determined by using standard curves (or other standard results). This technique is well-known.

For purposes of this invention, both monoclonal antibodies and polyclonal antibodies may be used in the immunoassays, as long as such antibodies possess the requisite specificity for the antigen of interest (e.g., vancomycin). The term "antibody," as used herein, refers to immunoglobulins that are produced in response to the detection of a foreign substance, and includes intact molecules, as well as functional fragments thereof, such as Fab, $F(ab')_2$ and Fv. In a preferred embodiment, the immunoassays of the present invention employ monoclonal antibodies. Most preferably, such antibodies are generated by immunizing a mouse, rat, rabbit, etc. with the analyte of interest conjugated to an antigenic protein, or in concert with an adjuvant, harvesting the splenic leukocytes of the animal, and fusing them with a suitable myeloma cell. Preferably, the monoclonal antibody has negligible cross-reactivity to vancomycin degradation product(s) (See FIG. 1). The antibody can be diluted, for example, in PBS (20 mM, pH 7) before use.

The immunoassays of the present invention can be antibody-triggered or conjugate-triggered. For example, in an antibody-triggered assay, the stabilized vancomycin conjugate formulation and the test sample are first combined to form a mixture. The anti-vancomycin antibody is then added to the mixture to trigger competitive immune complex formation.

Alternatively, in a conjugate triggered assay, the test sample and anti-vancomycin antibody are first combined to form a mixture, and then the stabilized vancomycin conjugate formulation is added to the mixture to trigger immune complex formation.

The stabilized vancomycin conjugate formulations of this invention provide acceptable stability in both the dose-response curve and reaction rate of immunoassays employing the conjugate formulation. Further, immunoassays using this formulation have lower non-specific reaction rates.

The inventors also surprisingly and unexpectedly discovered that in addition to acting as a stabilizing agent for the vancomycin conjugate formulations, DALAA also modulates the dose-response curve in particle-based homogenous vancomycin assays, as discussed below in Example 7. That is, the inclusion of DALAA permits one to modulate the sensitivity of immunoassays so as to obtain an assay that exhibits a more desirable reaction rate and dose response. As used herein, a "dose response modulator" is any compound that will produce in particular the following "desired assay parameters" in immunoassays:

(1) a rate of greater than or equal to about 0.3 ΔO.D. units/minute at an analyte concentration of 0 μg/mL (the term "O.D." denotes optical density or absorbance);

(2) a reaction rate of greater than about 0.02Δ (O.D. units)/minute at the highest calibrator concentration;

(3) a dose response (as represented by "% $B/B_o$") of about 75–85% at the lowest non-zero calibrator concentration, and of less that 25% at the highest calibrator concentration. The term "% $B/B_o$" denotes the percentage of the ratio of the rate at a particular concentration to the initial rate;

(4) a dose response curve with good separation in reaction rate (>=0.03 ΔO.D. units) between any two calibrator concentrations;

(5) a capacity to measure analyte concentrations across an entire physiologically or otherwise relevant assay measuring range.

The inclusion of DALAA in the stabilized vancomycin conjugate formulations of this invention permits the modulation or adjustment of the dose response curve in immunoassays in order to achieve the above-described parameters and, hence, acceptable precision and accuracy.

The inventors of the present invention also surprisingly and unexpectedly discovered that when heparin is included in the vancomycin conjugate formulations of this invention, the non-specific reaction rate or particle-enhanced immunoassays was lowered. Further, increasing the amount of heparin was found to steepen the dose response with a concomitant decrease of rate unit. These beneficial effects caused by the addition of heparin to the formulation are possibly due to the reduction or elimination of intermolecular hydrogen bonding by charge interaction with vancomycin, since the heparin molecule is highly charged.

The assays disclosed herein may further include a novel rate enhancer and/or a novel dose response modulator of this invention. Conventional immunoassay formats often include polyethylene glycol (PEG) as a rate enhancer. However, PEG is quite viscous, and can cause poor assay precision when used in high concentration. The inventors of the present invention discovered that the reaction rate of immunoassays of this invention could be enhanced by the addition of a low molecular weight amine such as ethylenediamine (EDA) as the rate enhancer. For example, it was discovered that substituting EDA for some or all of the PEG typically employed significantly enhances the rate of immune complex formation (see Example 6).

In addition, it was discovered that the low molecular weight amines such as EDA also act as dose response modulators. That is, the inclusion of low molecular weight amines such as EDA permits one to modulate the sensitivity of immunoassays so as to obtain an assay that exhibits a more desirable reaction rate and dose response as discussed above.

This novel application of EDA as a rate enhancer and a dose response modulator has advantages over the conventionally-used polyethylene glycol (PEG) and other rate enhancers and dose response modulators. For example, EDA is a simple chemical (MW 133) and is not subjected to performance changes as a result of purity and grade changes from lot to lot, as has been known for PEG. Furthermore, EDA is not viscous like PEG and, therefore, substituting EDA for some or all of the PEG as a rate enhancer avoids the poor assay precision observed when PEG is used as the sole rate enhancer or dose response modulator. Other low molecular weight amines suitable for use as rate enhancers and dose response modulators include 1,3-diaminopropane and 1,2-diaminopropane.

Although the improvement resulting from the use of low molecular weight amines as rate enhancers and dose response modulators has been described herein for bidentate-based particle enhanced immunoassays, the use of these low molecular weight amines is not limited to such assays. Thus, this invention also includes the use of low molecular weight amines as rate enhancers and dose response modulators in any assay for the detection and/or quantitation of an analyte in a test sample. As used herein, an "analyte" refers to the substance whose presence and/or concentration in a sample is to be determined. The term "analyte" includes any substance for which there exists a specific binding molecule, or for which a specific binding molecule can be prepared. Representative analytes include, but are not limited to, drugs, antigens, haptens, antibodies, proteins, peptides, amino acids, hormones, steroids, cancer cell markers, tissue cells, viruses, vitamins, nucleic acids, and pesticides.

When employed as a rate enhancer in a vancomycin assay according to the method of this invention, EDA can be formulated into either the conjugate diluent or preferably the reaction buffer. It can be used as the only rate enhancer in the assay, or in combination with other rate enhancers such as PEG. There was also a strong indication that EDA could also serve to improve the recovery of low concentration vancomycin calibrators containing between about 5 to 50 µg/mL vancomycin. These calibrators are used in preparing dose-response curves (see Example 6).

Alternatively, the assays of this invention may include a detergent as a dose response modulator. The use of detergents as dose response modulators in immunoassay formats is described by Cheng et al. in U.S. Pat. No. 5,627,080, which is specifically incorporated herein by reference. The detergents that may be employed in accordance with the methods of the present invention include anionic detergents, cationic detergent(s), zwitterionic detergents and nonionic detergents. The detergents may be added to the conjugate diluent buffer or to the antibody diluent.

The stabilized vancomycin conjugate formulation may be incorporated into a kit for use in immunoassays for vancomycin. Accordingly, another aspect of this invention provides a test kit for detecting the presence of vancomycin in a test sample, comprising a) an assay medium; b) a stabilized vancomycin conjugate formulation prepared according to the method of this invention, and c) an anti-vancomycin antibody. The reaction buffer may further include one or more rate enhancers such as EDA, PEG, or other polymeric enhancers. The kits may further include a dose response modulator such as a low molecular weight amine or a detergent. The stabilized vancomycin conjugate formulation comprises at least one stabilizing agent and is stored in suitable diluent. Tris buffer (20 mM, pH 7.5) or phosphate buffer (20 mM, pH 7) are examples of suitable conjugate diluents for the conjugate formulation. The conjugate diluent preferably also contains detergent, heparin and BSA. Preferably, the antibody is a monoclonal antibody with negligible cross-reactivity with a vancomycin degradation product (See FIG. 1).

Mixing of the kit components results in turbidity change, due to specific aggregation of vancomycin-immobilized particles by the antibody. Vancomycin, if present in a sample, binds to the antibody, and inhibits particle aggregation. Thus, increasing vancomycin concentration in a sample decreases turbidity, and the inverse vancomycin dose—turbidity relationship allows the quantitation of vancomycin in a sample. Either the vancomycin conjugate or the antibody can be used as the trigger conjugate for the aggregation reaction.

Having now generally described the invention, the same will be more readily understood through reference to the following examples, which are provided by way of illustration, and are not intended to be limiting of the present invention.

EXAMPLES

Example 1

Preparation of an Avidin-Latex Particle

In a particularly preferred method for coupling these reagents, carboxylated latex was suspended in a solution of approximately 0.1M [3(N-morpholino)] propanesulfonic acid ("MOPS") (pH 6.0), approximately 0.5% polyoxyethylene (20) sorbitan ("Tween-20") (pH 6). The suspension was cooled to approximately 4° C. and provided with ⅛ volume of cold 0.1M MOPS (pH 6) containing 63 mg/ml of N-hydroxysuccinimide. One-tenth volume of 0.1M MOPS (pH 6) containing 46 mg/ml of a water soluble carbodiimide was then added. The resulting mixture was then adjusted to pH 5.5–6, and stirred for approximately 1 hour at about 4° C. Thereafter, the pH was raised to about 9, and the reactants were permitted to react for an additional 5 hours with about 2 volumes of cold 0.02M borate buffer (pH 9) containing dissolved avidin at about 0.6 mg/ml.

BSA was then added to a final concentration of approximately 2 mg/ml, and the solution was stirred overnight at about 4° C. After this incubation, the latex-avidin mixture was dialyzed against 3 changes of 0.02M Tris (pH 9) buffer, containing 0.2% Tween-20 for 1.5 days, and purified, either by passage through a sepharose CL-6B column, or by other means (such as the Pellicon Cassette System (PCS)), and membrane having a molecular weight cutoff (MWCO) of 300 K. Such avidin-labeled particles may be used in conjunction with any of the immunoassay formats described herein that employ a biotinylated bidentate reagent.

Heat-stressing the latex-avidin before coupling to the bidentate or the latex-avidin-bidentate conjugate itself for 3 to 6 days at 45° C. enhances the immunoreactivity and assay sensitivity in terms of steeper dose response.

Example 2

Preparation of a Vancomycin Bidentate

Triethylamine (2 mL) was added to a DMF solution (30 mL) containing vancomycin hydrochloride (1 g), biotinlyated amine (biotin-hexanediamine-aminocaproic acid, 0.4 g), and N-hydroxybenzothiazole (200 mg). After addition of 1,3-dicyclohexylcarbodiimide (1.48 g), the mixture was heated at 50° C. for 10 h and then left at ambient temperature for overnight. The solvent was evaporated to dryness. The residue was eluted on a silica gel column firstly using ethyl acetate:methanol:dichloromethane:ammonium hydroxide (6:6:2:1.2 by volume), and then 5–7% by volume of ammonium hydroxide in methanol. The ammonium-methanol fractions containing vancomycin bidentate was pooled, and the solvent was evaporated to give the solid vancomycin bidentate (yield: 0.16 g).

Example 2A

Coupling the Vancomycin Bidentate to the Avidin Particles

To 500 mL of latex-avidin solution at pH 9 was added with stirring a solution of 14 mg of vancomycin bidentate in 2.8 mL of DMF. The solution was stirred at ambient temperature for 1 h after which the mixture was washed by ultrafiltration to remove the excess bidentate and other small molecules using 20 mM TRIS containing 0.2% Tween-20 at pH 9. After ultrafiltration and concentration to 80% volume (400 mL), BSA (0.2 mg/mL), sodium heparin (2.295 g, 1000 units/mL) and DALAA (100 to 500 mg) were added to the conjugate at pH 9 or with the pH adjusted to pH 7.5. The conjugate was subsequently heat stressed at 45° C. for up to 9 days at either pH or for a time period until acceptable dose response or stability was achieved. The conjugate could be stored at pH 9 or preferably at about pH 7.5 for better storage stability.

Example 3

Effect of DALAA and Heparin on Vancomycin Conjugate Formulation Stabilization

This study utilized 230 $\mu$L reaction buffer, 40 $\mu$L sample, 40 $\mu$L antibody, and 32 $\mu$L of a stabilized vancomycin conjugate formulation in an antibody-triggered assay. After mixing the sample and conjugate in the reaction buffer, the reaction was triggered by adding the antibody, and the turbidity change monitored at 340 nm on the Synchron CX® System (Beckman Coulter). The reaction buffer contained 3% Triton X-100 and 3% PEG.

Table 1 shows the effect of heparin in the stabilized vancomycin conjugate formulation containing 100 molar excess of the tripeptide Nα, Nβ-diacetyl-L-lysine-D-alanine-D-alanine (DALAA) on the non-specific reaction rate, specific reaction rate, and dose response before heat-stressing. Increasing the amount of heparin from 1000 to 1500 units resulted in lowering of the non-specific reaction rate, and deepening of the dose response, with a concomitant decrease of the rate unit. The dose response is represented as % $B/B_o$, that is, the percentage of the ratio of an indicated rate relative to the initial reaction rate.

TABLE 1

Effect of heparin on specific and non-specific rates, and dose response

| Vancomycin ($\mu$g/mL) | Heparin in vancomycin-conjugate formulation | |
|---|---|---|
| | 1000 Units | 1500 Units |
| Specific Rate Unit | | |
| 0 | 0.49156 | 0.34829 |
| 5 | 0.42785 | 0.27907 |
| 10 | 0.34805 | 0.19600 |
| 20 | 0.21084 | 0.09790 |
| 30 | 0.15268 | 0.07131 |
| 50 | 0.11562 | 0.05759 |
| Non-Specific Rate Unit | | |
| 0–50 | 0.03700 | 0.0200 |
| % $B/B_o$ | | |
| 0 | 100.0 | 100.0 |
| 5 | 84.6 | 89.4 |
| 10 | 66.6 | 61.9 |
| 20 | 34.0 | 28.4 |
| 30 | 19.4 | 14.0 |
| 50 | 11.5 | 9.3 |

Table 2 shows the increase of the non-specific reaction rate and perturbation of the specific reaction rate by the tripeptide DALAA, in the conjugate before heat-stressing.

TABLE 2

Effect of tripeptide on non-specific and specific reaction rates

| Vancomycin ($\mu$g/mL) | Without Tripeptide | With 100X Tripeptide |
|---|---|---|
| Specific Rate Unit | | |
| 0 | 0.54659 | 0.49156 |
| 5 | 0.49302 | 0.42785 |
| 10 | 0.39906 | 0.34805 |
| 20 | 0.22065 | 0.21804 |
| 30 | 0.15783 | 0.15268 |
| 50 | 0.11634 | 0.11562 |
| Non-Specific Rate Unit | | |
| 0–50 | ~0.02 | ~0.036 |

Example 4

Stability of Vancomycin Conjugate Formulation after Heat-Stressing

This study utilized 230 $\mu$L reaction buffer, 4 $\mu$L sample, 40 $\mu$L antibody, and 32 $\mu$L stabilized vancomycin conjugate formulation in an antibody triggered assay. After mixing the sample and conjugate in the reaction buffer, the reaction was triggered by adding the antibody, and the turbidity change monitored at 340 nm on the Synchron CX® System (Beckman Coulter). The reaction buffer contained 3% Triton X-100 and 3% PEG.

Figure 3:
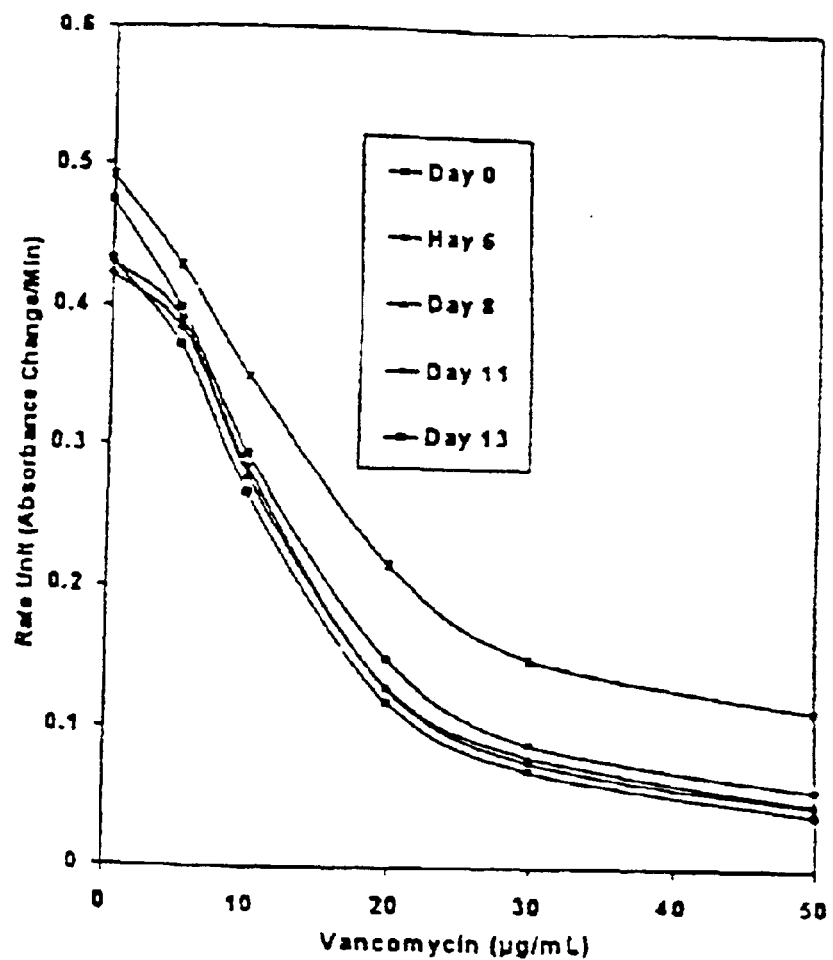
FIG. 3 is a plot of the stability of a vancomycin conjugate of this invention after heat-stressing the conjugate, presented as rate units (Absorbance change/minute) versus vancomycin concentration. Days 0, 6, 8, 11 and 13 represent the number of days the conjugate was heated.

Table 3 and FIG. 3 demonstrate the effect of heat-stressing the vancomycin conjugate formulation at 45° C. for 6 days in the presence of 100 molar excess of the tripeptide and 1000 units/mL of heparin at pH 7.5. In the first 6 days post heat pretreatment, a significant lowering of the non-specific rate was attained and a substantial increase in dose response was observed. In the next 7 days post heat pretreatment, the non-specific reaction rate remained low, and the dose-response became stabilized to an acceptable level, with the $B_o$ rate dropping by just 10%. Thus, the stability of the stabilized vancomycin conjugate formulation in terms of the rate unit and dose response after 6 days of heat pretreatment is at least 7 days at 45° C., equivalent to greater than 18 months at 4° C.

TABLE 3

Stability of vancomycin conjugate formulation post heat pretreatment.

| Vancomycin | No. Days Heat-Stressing at 45° C. at pH 7.45 | | | | |
|---|---|---|---|---|---|
| (µg/mL) | 0 | 6 | 8 | 11 | 13 |
| | Specific Rate Unit | | | | |
| 0 | 0.49156 | 0.47375 | 0.43158 | 0.42261 | 0.43193 |
| 5 | 0.42785 | 0.39818 | 0.39032 | 0.38355 | 0.37121 |
| 10 | 0.34805 | 0.29338 | 0.27816 | 0.28392 | 0.26577 |
| 20 | 0.21084 | 0.15262 | 0.13304 | 0.13169 | 0.12181 |
| 30 | 0.15268 | 0.09021 | 0.08147 | 0.07712 | 0.07061 |
| 50 | 0.11562 | 0.05682 | 0.04667 | 0.04408 | 0.03857 |
| | Non-Specific Rate Unit | | | | |
| 0–50 | ~0.03700 | ~0.011 | ~0.008 | ~0.005 | ~0.005 |
| | % $B/B_o$ | | | | |
| 0 | 100.0 | 100.0 | 100.0 | 100.0 | 100.0 |
| 5 | 87.0 | 84.0 | 90.4 | 90.8 | 85.9 |
| 10 | 70.8 | 61.9 | 64.5 | 67.2 | 61.5 |
| 20 | 44.4 | 32.2 | 30.8 | 31.2 | 28.2 |
| 30 | 31.1 | 19.0 | 18.9 | 18.2 | 16.3 |
| 50 | 23.5 | 12.0 | 10.8 | 10.4 | 8.9 |

Example 5

Effects of pH on Stability of Vancomycin Conjugate Formulation

This study utilized 230 µL reaction buffer, 4 µL sample, 40 L antibody, and 32 µL stabilized vancomycin conjugate formulation in an antibody triggered assay. After mixing the sample and conjugate in the reaction buffer, the reaction was triggered by adding the antibody, and the turbidity change monitored at 340 nm on the Synchron CX® System (Beckman Coulter). The reaction buffer contained 3% Triton X-100 and 3% PEG.

Table 4 illustrates the effect of neutral and alkaline pH on the heat stability of vancomycin conjugate formulations in the presence of about 200 molar excess of the vancomycin complexing agent DALAA. As the results indicate, vancomycin conjugate formulation stabilization to heat-stressing was achieved for an extensive time period at close to neutral pH, but not at alkaline pH, even in the presence of huge excess of the tripeptide. With the 9 day heat pre-treatment, conducted at pH 9 in the presence of the tripeptide and the storage buffer also at pH 9, the reaction rate dropped as much as 59% after 7 days at 45° C. However, if both the heat pretreatment and storage were at pH 7.5, acceptable immunoreactivity and dose response were achieved.

TABLE 4

Stability of vancomycin conjugate formulation at 45° C.

| | 9 Days of Heat Pretreatment at 45° C. at pH 9.0 Storage Buffer pH = 9.0 No Days at 45° C. Post Heat Pretreatment | | | 9 Days of Heat Pretreatment at 45° C. at pH 7.5 Storage Buffer pH = 7.5 No Days at 45° C. Post Heat Pretreatment | | |
|---|---|---|---|---|---|---|
| Vancomycin | | | | | | |
| (µg/mL) | 0 | 4 | 7 | 0 | 4 | 7 |
| | Specific Rate Unit | | | Specific Rate Unit | | |
| 0 | 0.35236 | 0.19301 | 0.13617 | 0.48785 | 0.48453 | 0.47933 |
| 5 | 0.25999 | 0.12240 | 0.09793 | 0.40288 | 0.38987 | 0.38825 |
| 10 | 0.18013 | 0.07514 | 0.06390 | 0.32158 | 0.30601 | 0.30065 |
| 20 | 0.06557 | 0.02972 | 0.02538 | 0.19987 | 0.17871 | 0.17300 |
| 30 | 0.03284 | 0.01776 | 0.01561 | 0.13979 | 0.12416 | 0.11929 |
| 50 | 0.01404 | 0.00865 | 0.00698 | 0.09440 | 0.08225 | 0.07792 |
| | Non-Specific Rate Unit | | | Non-Specific Rate Unit | | |
| 0–50 | 0.001 | 0.0007 | 0.0003 | 0.06 | 0.03 | 0.03 |
| | % $B/B_o$ | | | % $B/B_o$ | | |
| 0 | 100.0 | 100.0 | 100.0 | 100.0 | 100.0 | 100.0 |
| 5 | 73.8 | 63.4 | 71.9 | 82.6 | 80.5 | 81.0 |
| 10 | 51.1 | 38.9 | 46.9 | 65.9 | 63.2 | 62.7 |
| 20 | 18.6 | 15.4 | 18.6 | 41.0 | 36.9 | 36.1 |
| 30 | 9.3 | 9.2 | 11.5 | 28.7 | 25.6 | 24.9 |
| 50 | 4.0 | 4.5 | 5.1 | 19.4 | 17.0 | 16.3 |

Example 6

Particle-Based Homogeneous Vancomycin Assay on Synchron CX® and Synchron LX® Systems Employing Stable Vancomycin Conjugate Formulation, and Ethylenediamine as a Novel Rate Enhancer and Dose Response Modulator The effect of ethylenediamine (EDA) on the reaction rate and dose-response curve of an immunoassay using a vancomycin conjugate formulation of this invention was examined. In one assay, EDA (10 mM) was incorporated in the reaction buffer, and the reaction buffer contained 2.5% PEG and 2.5% Triton X-100 in both cases. This assay was compared to an assay without EDA. The results are summarized in Table 5.

As the results indicate, the reaction rate was greatly enhanced and the dose response modulated as the concentration of EDA was increased. This novel application of EDA as a rate enhancer has advantages over the conventionally-used polyethylene glycol (PEG) and other rate enhancers, as EDA is a simple chemical (MW 133), and is not subjected to performance changes as a result of purity and grade changes from lot to lot as has been known for PEG. Furthermore, PEG is quite viscous, and can cause poor assay precision when used in high concentration.

There was also a strong indication, as illustrated in Table 6, that EDA could serve to improve the recovery of the low concentration vancomycin calibrator (5 µg/mL) on the Synchron LX®.

When employed as a rate enhancer in the vancomycin assay, EDA can be formulated in either the conjugate diluent or, preferably, the reaction buffer. It can be used as the only rate enhancer in the assay, or in combination with other rate enhancers like PEG. EDA, PEG and Triton X-100 were added in the reaction buffer in this example.

TABLE 5

Effect of ethylenediamine (EDA) on the reaction
rate and dose-response curve in
a conjugate-triggered assay.

| Vancomycin | 0 mM EDA | | 10 mM EDA | |
|---|---|---|---|---|
| (µg/mL) | Rate | % B/B$_o$ | Rate | % B/B$_o$ |
| 0 | 0.17480 | 100.0 | 0.63110 | 100.0 |
| 5 | 0.14369 | 82.2 | 0.52060 | 82.5 |
| 10 | 0.11110 | 63.6 | 0.42894 | 68.0 |
| 20 | 0.06258 | 35.8 | 0.28167 | 44.6 |
| 30 | 0.03671 | 21.0 | 0.18013 | 28.5 |
| 50 | 0.01257 | 7.2 | 0.07779 | 12.3 |

TABLE 6

Effect of ethylenediamine on the recovery of low level vancomycin calibrators
in a conjugate-triggered assay.

Calibration Reaction Rate

| | Experiment 1 | | Experiment 2 | | |
|---|---|---|---|---|---|
| | LX No 1 | | LX No 1 | | LX No 2 |
| Vancomycin Calibrator µg/mL | No EDA (2% PEG) (3% Triton X-100) | 10 mM EDA (1% PEG) (2.5% Triton X-100) | No EDA (2% PEG) (3% Triton X-100) | 10 mM EDA (1% PEG) (2.5% Triton X-100) | 10 mM EDA (1% PEG) (2.5% Triton X-100) |
| 0 | 0.3598 | 0.3562 | 0.4536 | 0.4265 | 0.4621 |
| 5 | 0.2161 | 0.2196 | 0.2794 | 0.3206 | 0.3178 |
| 10 | 0.1540 | 0.1534 | 0.2284 | 0.2297 | 0.2315 |
| 20 | 0.0733 | 0.0619 | 0.0982 | 0.1048 | 0.1074 |
| 30 | 0.0289 | 0.0309 | 0.0465 | 0.0454 | 0.0498 |
| 50 | 0.0060 | 0.0180 | 0.0115 | 0.0216 | 0.0257 |

Recovery of Calibrators Run as Samples

| Target µg/mL | µg/mL | µg/mL | µg/mL | µg/mL | |
|---|---|---|---|---|---|
| 0 | 0.1 | 0.1 | 0.1 | 0.1 | 0.1 |
| 0 | 0.1 | 0.1 | 0.1 | 0.1 | 0.4 |
| 0 | 0.1 | 0.1 | 0.1 | 0.1 | 0.2 |
| 5 | 3.5 | 4.3 | 2.8 | 4.6 | 5.0 |
| 5 | 3.7 | 5.1 | 3.0 | 4.6 | 4.8 |
| 5 | 3.3 | 5.1 | 3.0 | 4.6 | 5.2 |

Example 7

Figure 4:
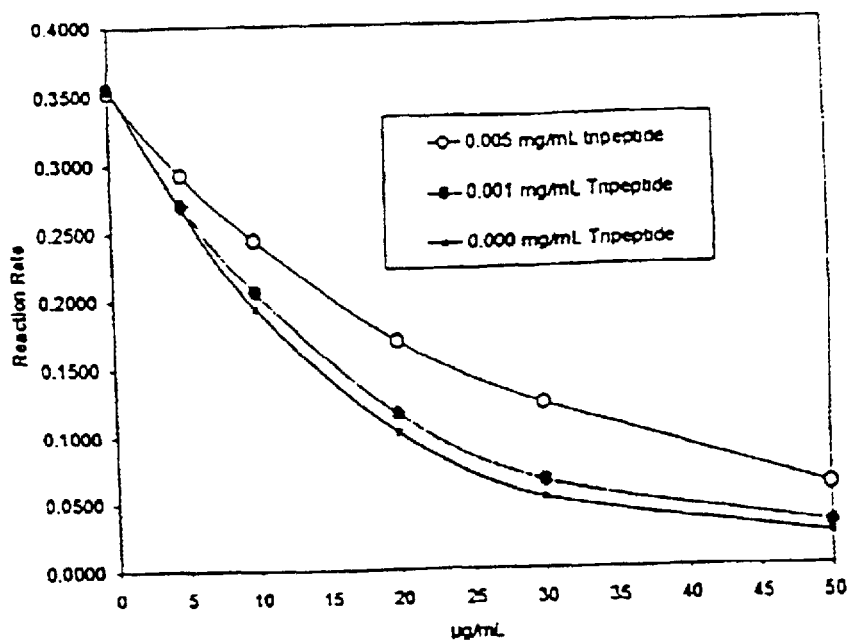
FIG. 4 is a plot of the modulation of the dose response of an immunoassay employing a stabilized vancomycin conjugate of this invention stabilized with DALAA, presented as rate units versus vancomycin concentration.

Particle-Based Homogeneous Vancomycin Assay on Synchron CX® and Synchron LX® Systems Employing Stabilized Vancomycin Conjugate Formulation, Ethylenediamine as the Rate Enhancer, and a Vancomycin Complexing Agent as Dose-Response Modulator The vancomycin-complexing agent Nα,Nβ-diacetyl-L-lysine-D-alanine-D-alanine (DALAA) not only serves to stabilize the vancomycin conjugate formulation, but can also be utilized to modulate the dose-response curve. An example of the vancomycin-complexing agent's modulation property, when incorporated in the reaction buffer, is given in Table 7 and FIG. 4. In this example, the reaction buffer: 2.5% PEG, 2% Triton X-100, 10 mM ethylenediamine, and various concentrations of DALAA. The assay was conjugate triggered.

When no binding agent was used, the absorbance span between the 30 µg/mL and 50 µg/mL concentration levels was only about 20 milli-absorbance units, and such small absorbance span could result in poor assay precision in this concentration range. In the presence of 0.005 mg/mL binding agent, the absorbance span was increased to about 60 milli-absorbance units, and the larger absorbance span would certainly allow more accurate quantitation at these levels.

TABLE 7

Modulation of dose response using DALAA.

DALAA in Reaction Buffer

| Vancomycin | 0 mg/mL | | 0.001 mg/mL | | 0.005 mg/mL | |
|---|---|---|---|---|---|---|
| (µg/mL) | Rate | % B/B$_o$ | Rate | % B/B$_o$ | Rate | % B/B$_o$ |
| 0 | 0.3576 | 100.0 | 0.3559 | 100.0 | 0.3527 | 100.0 |
| 5 | 0.2665 | 74.5 | 0.2699 | 75.8 | 0.2917 | 82.7 |
| 10 | 0.1936 | 54.2 | 0.2059 | 57.8 | 0.2439 | 69.1 |

TABLE 7-continued

Modulation of dose response using DALAA.

| Vancomycin | DALAA in Reaction Buffer | | | | | |
|---|---|---|---|---|---|---|
| | 0 mg/mL | | 0.001 mg/mL | | 0.005 mg/mL | |
| (μg/mL) | Rate | % B/B$_o$ | Rate | % B/B$_o$ | Rate | % B/B$_o$ |
| 20 | 0.1021 | 28.6 | 0.1156 | 32.5 | 0.1684 | 47.8 |
| 30 | 0.0532 | 14.9 | 0.0652 | 18.3 | 0.1222 | 34.7 |
| 50 | 0.0233 | 6.5 | 0.0310 | 8.7 | 0.0591 | 16.8 |

Example 8

Assay Performance Results

Figure 5:
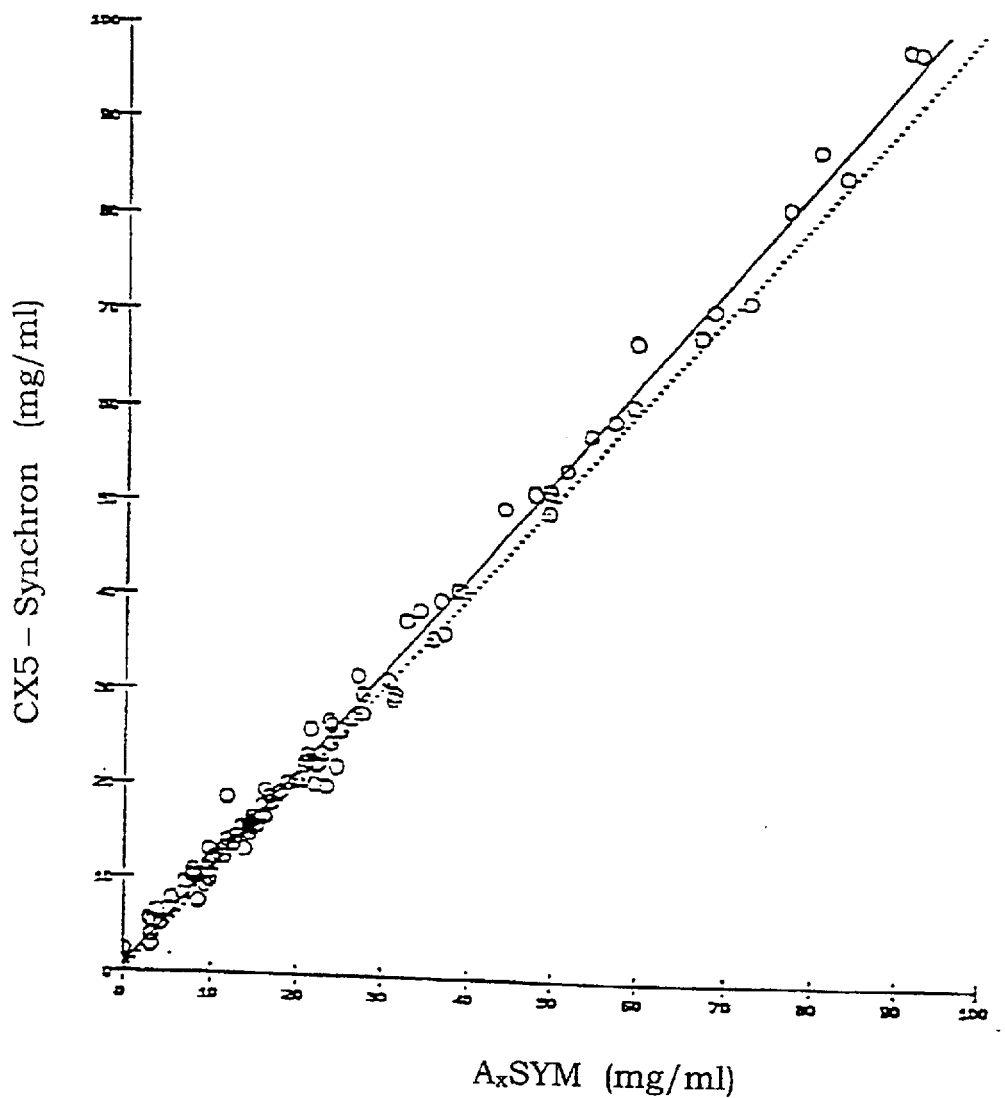
FIG. 5 illustrates the correlation results between the CX5 Synchron® System (Beckman Coulter) and a fluorescence polarization assay using the AxSYM® System (Abbott).

Patient Sample Correlation—A method comparison study using a fluorescence polarization assay as the comparative method on 95 samples gave the correlation results shown in FIG. 5, which indicated a slope of 1.035, an intercept of 0.6 and a correlation coefficient of 0.996. This study utilized 0.005 mg/mL of the tripeptide DALAA in the reaction buffer. The assay was antibody-triggered method. The analytical range was 5 to 100 μg/mL.

Figure 6A:
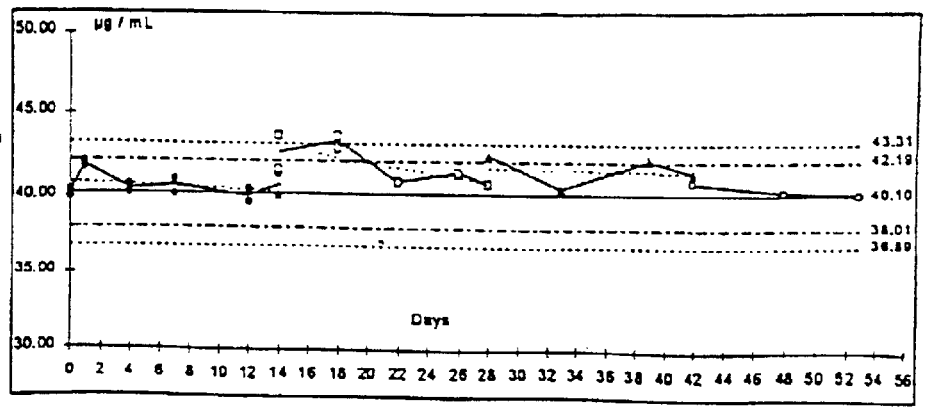
FIGS. 6A–6C represent the on-instrument stability of the vancomycin conjugates of this invention on the CX5 Synchron® System.
Figure 6B:
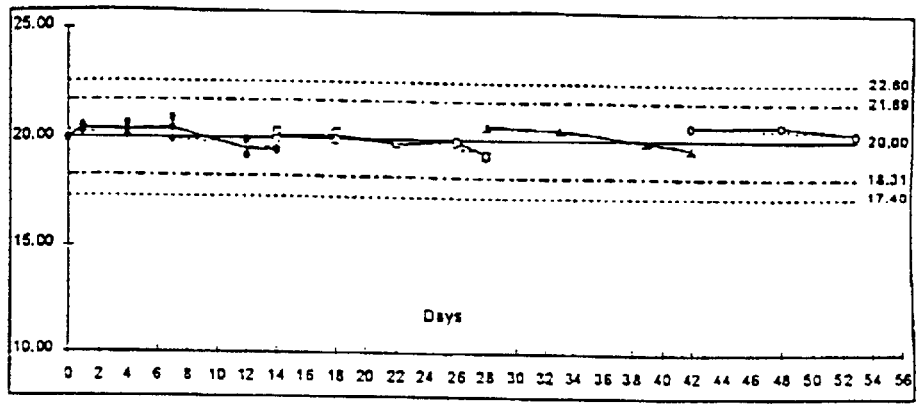
Figure 6C:
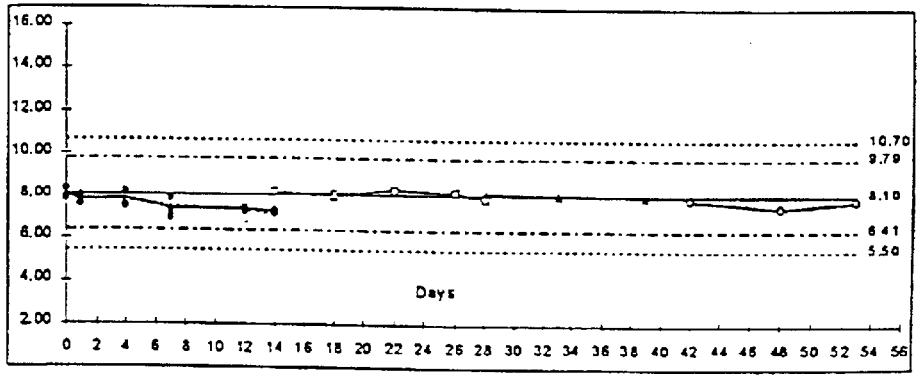

Calibration Frequency/On-Instrument Stability of a Stabilized Vancomycin Conjugate Formulation The calibration frequency and on-instrument stability of the stabilized vancomycin conjugate formulations is shown in FIGS. 6A–6C, which exhibited four calibration cycles of 14 days for each of the first three cycles, and 11 days for the fourth cycle, with calibration performed on the first day of each cycle. The assay was conjugate-triggered, with an analytical range of 5 to 50 μg/mL and with 10 mM ethylenediamine (EDA) incorporated in the reaction buffer. Based on the result, a calibration frequency of 14 days, and an on-instrument stability of 53 days was achieved. "On-instrument stability" denotes the length of time that a stabilized vancomycin conjugate formulation of this invention can be maintained in an opened cartridge and still provide acceptable performance.

The invention may be embodied in other specific forms without departing from its essential characteristics. The described embodiments are to be considered in all respects only as illustrative and not as restrictive. Indeed, those skilled in the art can readily envision and produce further embodiments, based on the teachings herein, without undue experimentation. The scope of the invention is, therefore, indicated by the appended claims rather than by the foregoing description. All changes that come within the meaning and range of the equivalence of the claims are to be embraced within their scope.

We claim:

1. A stabilized vancomycin conjugate prepared by a method comprising:
   (a) forming a vancomycin conjugate comprising a vancomycin member bound to a ligand, said ligand being bound to a ligand-binding partner immobilized on a solid support, wherein said conjugate is formed under conditions that minimize intermolecular hydrogen bonding between vancomycin members;
   (b) mixing said conjugate with at least one stabilizing agent that prevents dimerization of said vancomycin member, wherein the pH of the mixture is between about pH 7 to pH 9;
   (c) heating the mixture at a temperature between about 40° and 50° C. for about 3 to 14 days to ensure colloidal stability; and
   (d) storing the heat-treated mixture obtained in step (c) in a diluent buffer having a pH of about 6.5 to 8.5.

2. The stabilized vancomycin conjugate of claim 1, wherein said conjugate has a heat-stressed stability of about seven days at about 45° C.

3. The stabilized vancomycin conjugate of claim 1, wherein said stabilized vancomycin conjugate has a shelf life of about eighteen months at about 4° C.

4. The stabilized vancomycin conjugate of claim 1, wherein said stabilized vancomycin conjugate has an on-instrument stability of 53 days.

5. A stabilized vancomycin conjugate formulation, comprising:
   a) a bidentate conjugate comprising a glycopeptide antibiotic vancomycin member bound to a ligand, said ligand being bound to a ligand-binding partner immobilized on a solid support; and
   b) at least one stabilizing agent that prevents dimerization of said vancomycin member, wherein said bidentate conjugate and said stabilizing agent are dissolved in a diluent buffer having a neutral pH.

6. The stabilized glycopeptide antibiotic vancomycin conjugate formulation of claim 5, wherein said stabilizing agent is selected from the group consisting of Nα,Nβ-diacetyl-L-lysine-D-alanine-D-alanine, heparin, acteyl-D-alanine-D-alanine and acetyl-D-alanine-D-alanine-D-alanine.

7. The stabilized vancomycin conjugate formulation of claim 5, wherein said solid support is a carrier particle selected from the group consisting of latex particles, metallic particles, colloidal metals and colloidal metal oxides.

8. The stabilized vancomycin conjugate formulation of claim 7, wherein said carrier particles are latex particles.

9. The stabilized vancomycin conjugate formulation of claim 8, wherein said latex particles having said ligand binding partner immobilized thereon are heat-stressed.

10. The stabilized vancomycin conjugate formulation of claim 5, wherein said ligand is biotin.

11. The stabilized vancomycin conjugate formulation of claim 10, wherein said ligand-binding partner is selected from the group consisting of avidin, streptavidin, and an anti-biotin antibody.

12. The stabilized vancomycin conjugate formulation of claim 5, further comprising one or more rate enhancers selected from the group consisting of ethylenediamine, polyethylene glycol, 1,3 diaminopropane and 1,2-diaminopropane.

13. A stabilized vancomycin conjugate formulation for use in a homogeneous assay of vancomycin in a test sample, comprising a biotinylated vancomycin bound to a biotin-binding partner, said biotin-binding partner being immobilized on a solid support, wherein said vancomycin conjugate has a heat-stressed stability of at least 7 days at 45° C. or a shelf life of at least 18 months at 4° C.

14. The formulation of claim 13, further comprising at least one stabilizing agent that prevents dimerization of said vancomycin member.

15. The formulation of claim 14, wherein said stabilizing agent is selected from the group consisting of Nα,Nβ-diacetyl-L-lysine-D-alanine-D-alanine, heparin, acteyl-D-alanine-D-alanine and acetyl-D-alanine-D-alanine-D-alanine.

16. A test kit for detecting the presence of vancomycin in a test sample, comprising:
  a) an assay medium;
  b) a stabilized vancomycin conjugate formulation, comprising:
    (i) a bidentate conjugate comprising a vancomycin member bound to a ligand, said ligand being bound to a ligand-binding partner immobilized on a solid support; and
    (ii) at least one stabilizing agent that prevents dimerization of said vancomycin member, wherein said bidentate conjugate and said stabilizing agent are dissolved in a conjugate diluent having a neutral pH; and
  c) an anti-vancomycin antibody.

17. The test kit of claim 16, wherein said stabilizing agent is selected from the group consisting of Nα,Nε-diacetyl-D-alanine-D-alanine-L-lysine, heparin, acteyl-D-alanine-D-alanine and acetyl-D-alanine-D-alanine-D-alanine.

18. The test kit of claim 16, further comprising one or more rate enhancers to enhance the binding of said antibody to said vancomycin in said sample or to said vancomycin member.

19. The test kit of claim 18, wherein said rate enhancer is selected from the group consisting of a lower molecular weight amine and a mixture of a lower molecular weight amine and polyethylene glycol.

20. The test kit of claim 18, wherein said lower molecular weight amine is selected from the group consisting of ethylenediamine, 1,2-diaminopropane and 1,3-diaminopropane.

21. The test kit of claim 16, further comprising a dose response modulator.

22. The test kit of claim 21, wherein said dose response modulator is selected from the group consisting of ethylenediamine, 1,2-diaminopropane 1,3-diaminopropane, Nα,Nε-diacetyl-D-alanine-D-alanine-L-lysine and a detergent.

23. The test kit of claim 16, wherein said ligand is biotin.

24. The test kit of claim 23, wherein said ligand-binding partner is selected from the group consisting of avidin, streptavidin, and an anti-biotin antibody.

25. The test kit of claim 16, wherein said assay medium is a TRIS buffer, a phosphate buffer, or a borate buffer.

26. The test kit of claim 16, wherein said solid support is carrier particles selected from the group consisting of latex particles, metallic particles, colloidal metals and colloidal metal oxides.

27. The test kit of claim 26, wherein said carrier particles are latex particles.

28. The test kit of claim 26, wherein said latex particles having said ligand binding partner immobilized thereon are heat-stressed.

* * * * *